US009631210B2

(12) United States Patent
Chou et al.

(10) Patent No.: US 9,631,210 B2
(45) Date of Patent: Apr. 25, 2017

(54) METHODS FOR INCREASING PRODUCTION OF 3-METHYL-2-BUTENOL USING FUSION PROTEINS

(75) Inventors: Howard Chou, Berkeley, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 390 days.

(21) Appl. No.: 14/345,147

(22) PCT Filed: Sep. 13, 2012

(86) PCT No.: PCT/US2012/055165
§ 371 (c)(1),
(2), (4) Date: Oct. 7, 2014

(87) PCT Pub. No.: WO2013/040210
PCT Pub. Date: Mar. 21, 2013

(65) Prior Publication Data
US 2015/0044747 A1 Feb. 12, 2015

Related U.S. Application Data

(60) Provisional application No. 61/534,816, filed on Sep. 14, 2011.

(51) Int. Cl.
*C12P 7/16* (2006.01)
*C12N 9/16* (2006.01)
*C12N 9/90* (2006.01)
*C12N 15/62* (2006.01)

(52) U.S. Cl.
CPC .............. *C12P 7/16* (2013.01); *C12N 9/16* (2013.01); *C12N 9/90* (2013.01); *C12N 15/62* (2013.01); *C12Y 503/03002* (2013.01); *Y02E 50/10* (2013.01)

(58) Field of Classification Search
CPC .... C12P 7/16; C12N 9/16; C12N 9/90; C12N 15/62
See application file for complete search history.

(56) References Cited

U.S. PATENT DOCUMENTS

2010/0205855 A1 8/2010 Chou et al.
2011/0046422 A1 2/2011 McAuliffe et al.
2011/0160501 A1 6/2011 Martin et al.

OTHER PUBLICATIONS

Bonanno et al.; "Structural genomics of enzymes involved in sterol/isoprenoid biosynthesis"; *Proc. Natl. Acad. Sci. USA*; 98:12896-12901 (2001).
Song, L.; "A soluble form of phosphatase in *Saccharomyces cerevisiae* capable of converting farnesyl diphosphate into E,E-farnesol"; *Appl. Biochem. Biotechnol.*; 128(2):149-158 (2006).
Street et al.; "Identification of Cys139 and Glu207 as catalytically important groups in the active site of isopentenyl diphosphate:dimethylallyl diphosphate isomerase"; *Biochemistry*; 33(14):4212-4217 (1994).

(Continued)

*Primary Examiner* — Alexander Kim
(74) *Attorney, Agent, or Firm* — Kilpatrick Townsend & Crew LLP

(57) ABSTRACT

The present invention relates to methods and compositions for increasing production of 3-methyl-2-butenol in a de novo synthetic pathway in a genetically modified host cell using isopentenyl disphosphate (IPP) as a substrate.

36 Claims, 3 Drawing Sheets

(56) References Cited

OTHER PUBLICATIONS

Wouters et al.; "Catalytic mechanism of *Escherichia coli* isopentenyl diphosphate isomerase involves Cys-67, Glu-116, and Tyr-104 as suggested by crystal structures of complexes with transition state analogues and irreversible inhibitors"; *J. Biol. Chem.*; 278(14):11903-11908 (2003) ePub Jan. 22, 2003.

Zhang et al.; "Crystal structures of human IPP isomerase: new insights into the catalytic mechanism"; *J. Mol. Biol.*; 366:1437-1446 (2007) ePub Nov. 3, 2006.

Zheng et al.; "The crystal structure of human isopentenyl diphosphate isomerase at 1.7 a resolution reveals its catalytic mechanism in isoprenoid biosynthesis"; *J. Mol. Biol.*; 366:1447-1458 (2007) ePub Dec. 24, 2006.

Laupitz et al.; "Stereochemical Studies on the Making and Unmaking of Isopentenyl Diphosphate in Different Biological Systems"; *Chemistry & Biodiversity*; 1:1367-1376 (2004).

The International Search Report and Written Opinion for PCT/US2012/055165, dated Feb. 12, 2013.

METHODS FOR INCREASING PRODUCTION OF 3-METHYL-2-BUTENOL USING FUSION PROTEINS

CROSS-REFERENCE TO RELATED APPLICATIONS

This application is the U.S. national stage of PCT/US2012/055165, filed Sep. 13, 2012, which claims benefit of U.S. provisional application No. 61/534,816, filed Sep. 14, 2011, each of which application is herein incorporated by reference for all purposes.

REFERENCE TO A SEQUENCE LISTING SUBMITTED AS AN ASCI TEXT FILE

This application includes a Sequence Listing as a text file named "SEQTXT_77429-889325.txt" created Mar. 14, 2014 and containing 11,665 bytes. The material contained in this text file is incorporated by reference.

STATEMENT AS TO RIGHTS TO INVENTIONS MADE UNDER FEDERALLY SPONSORED RESEARCH AND DEVELOPMENT

The invention described and claimed herein was made utilizing funds supplied by the U.S. Department of Energy under Contract No. DE-AC02-05CH11231. The government has certain rights in this invention.

BACKGROUND OF THE INVENTION

Petroleum derived fuels have been the primary source of energy for over a hundred years. Petroleum is formed over millions of years in nature and is a non-renewable source of energy. A significant amount of research in biofuels has been ongoing for decades. Within this field, ethanol has been studied intensively as a gasoline substitute. However, the efficiency of ethanol as a fuel remains debatable. (Pimentel, *Natural Resources Research* (2005) 14:65; Farrell et al., *Science* (2006), 311:506).

The alcohol 3-methyl-butanol has been demonstrated to be a potential biofuel in both spark-ignition and homogenous charge compression ignition (HCCI) engines. The compound can be synthesized from the isoprenoid pathway by converting the isoprenoid intermediate isoprenoid precursors isopentyl pyrophosphate (IPP) to dimethylallyl diphosphate (DMAPP), DMAPP to 3-methyl-2-butenol, and 3-methyl-2-butenol to 3-methyl-butanol (FIG. 1). The enzymes required for performing each individual step are: a phosphatase to convert IPP to 3-methyl-3-butenol, a phosphatase to convert DMAPP to 3-methyl-2-butenol, and a reductase to convert 3-methyl-2-butenol to 3-methyl-butanol. The enzymes can be expressed to obtain all of these three 5-carbon alcohols (see, e.g., U.S. Pat. No. 7,985,567, which is incorporated by reference). The conversion of IPP to DMAPP requires expression of an IPP isomerase.

The present invention relates to compositions and methods for expressing IPP isomerase as a fusion protein linked to a phosphatase to increase the production of 3-methyl-2-butenol from IPP and thus provides a method for increasing the production of 3-methyl 2-butenol for biofuel production.

BRIEF SUMMARY OF THE INVENTION

The invention relates, in part, to nucleic acid constructs, genetically modified host cells and methods employing such constructs and host cells to increase the production of 3-methyl-2-butenol from IPP.

Thus, in some aspects, the invention provides a genetically modified host cell transformed with a nucleic acid construct encoding a fusion protein comprising a phosphatase capable of catalyzing the dephosphorylation of dimethylallyl diphosphate (DMAPP) linked to an IPP isomerase capable of converting IPP to DMAPP, wherein the nucleic acid construct is operably linked to a promoter. In some embodiments, the genetically modified host cell further comprises a nucleic acid encoding a reductase that is capable of converting 3-methyl-2-butenol to 3-methyl-butanol. In some embodiments, the reductase is encoded by a nucleic acid construct introduced into the cell. In some embodiments, the IPP isomerase is a Type I isomerase. In some embodiments, the IPP isomerase is a Type II isomerase. In some embodiments, the host cell is selected from a group of taxonimcal classes consisting of *Escherichia*, *Enterobacter*, *Azotobacter*, *Erwinia*, *Bacillus*, *Pseudomonas*, *Klebsielia*, *Proteus*, *Salmonella*, *Serratia*, *Shigella*, *Rhizobia*, *Vitreoscilla*, *Synechococcus*, *Synechocystis*, and *Paracoccus* taxonomical classes. In some embodiments, the host cell is an *Escherichia coli* cell. In some embodiments, the host cell is a fungal cell, such as a yeast cell. In some embodiments, the yeast cell is a *Saccharomyces* sp. cell. In some embodiments, the host cell is an algal, insect or mammalian cell line. In some embodiments, the phosphatase is nudB from *E. coli*. In some embodiments, the IPP isomerase is encoded by an idi gene from *E. coli* or idi1 gene from *Saccharomyces cerevisiae*.

In a further aspect, the invention provides a method of producing 3-methyl-2-butenol in a genetically modified host cell of as described herein, wherein the genetically modified host cell comprises a nucleic acid construct encoding a fusion protein comprising a phosphatase capable of catalyzing the dephosphorylation of dimethylallyl diphosphate (DMAPP) linked to an IPP isomerase capable of converting IPP to DMAPP, the method comprising culturing the host cell under conditions such that the culturing results in the expression of the fusion protein and production of 3-methyl-2-butenol. In some embodiments, the method further comprises recovering 3-methyl-2-butenol produced by the cells. In some embodiments, the genetically modified host cell comprises a nucleic acid encoding a reductase such that expression of the reductase converts 3-methyl-2-butenol to 3-methyl butanol. In some embodiments, such a method further comprises recovering 3-methyl-2-butenol or 3-methyl butanol produced by the cells.

In an additional aspect, the invention provides a nucleic acid encoding a fusion construct comprising a phosphatase capable of catalyzing the dephosphorylation of dimethylallyl diphosphate (DMAPP) linked to an IPP isomerase capable of converting IPP to DMAPP. In some embodiments, the nucleic acid construct is operably linked to a promoter. In some embodiments, the nucleic acid construct is contained within an expression vector that is capable of replicating in a host cell. In some embodiments, the phosphatase is nudB from *E. coli*. In some embodiments, the IPP isomerase is encoded by an idi gene from *E. coli* or idi1 from *Saccharomyces cerevisiae*.

DETAILED DESCRIPTION OF THE INVENTION

Figure 1:
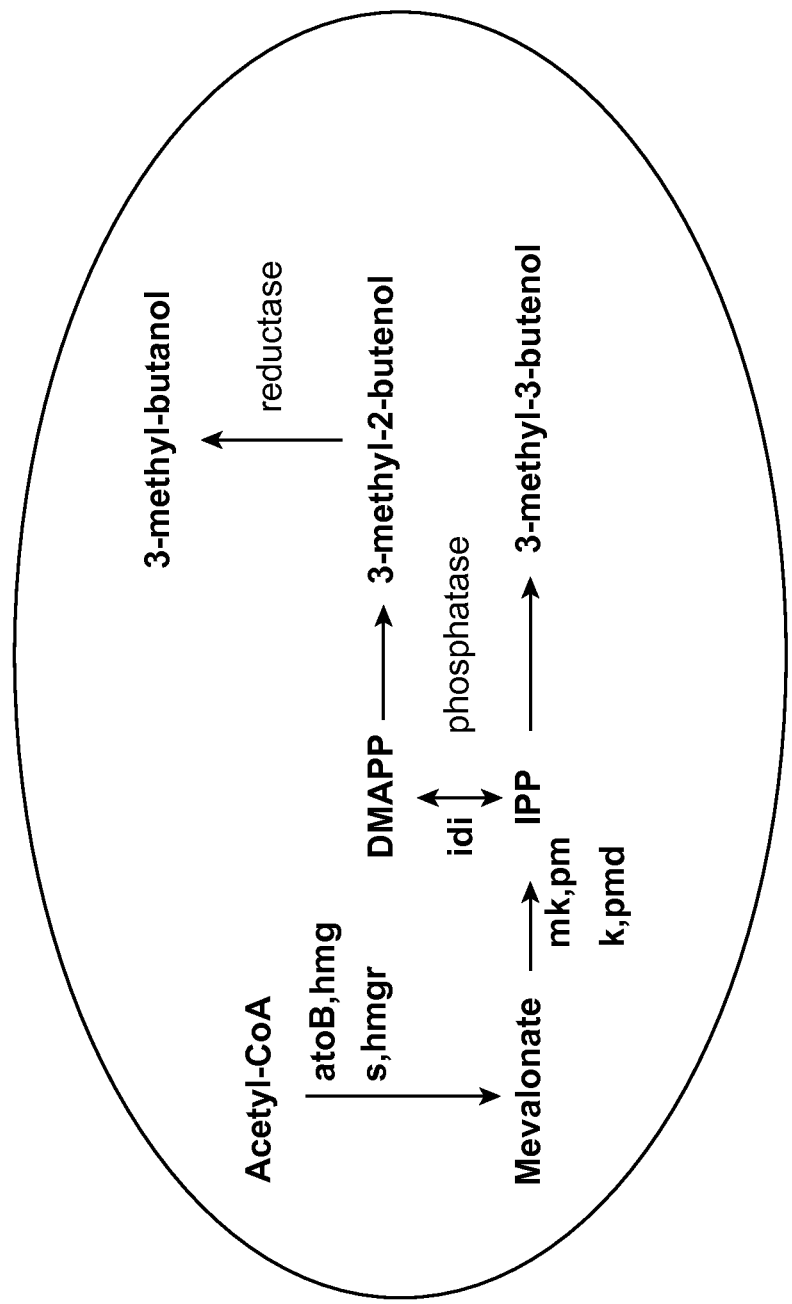
FIG. 1 provides a schematic depicting the synthesis of 3-methyl-butanol from the isoprenoid pathway by converting the isoprenoid intermediate IPP to DMAPP, DMAPP to 3-methyl-2-butenol, and 3-methyl-2-butenol to 3-methyl-butanol.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In order to more fully appreciate the invention the following definitions are provided.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

In the present invention, the terms "isopenty pyrophosate (IPP) isomerase", "IPP isomerase", "isopentenyl diphosphate isomerase, and "IDI" are used interchangeably to refer to an enzyme that catalyzes the interconversion of isopentenyl diphosphate (IPP) and dimethyl allyl diphosphate (DMAPP) (e.g., converting IPP into DMAPP and/or converting DMAPP into IPP). Standard methods such as those described herein and in the examples are used to assess whether a polypeptide has IPP isomerase activity by measuring the ability of the polypeptide to interconvert IPP and DMAPP in vitro, in a cell extract, or in vivo. Examples of IPP isomerase polypeptides and nucleic acids and methods of measuring IPP isomerase activity include, but are not limited to, those described in WO 2009/076676, U.S. Patent Application Publication No. 2009/0203102, WO 2010/003007, U.S. Patent Application Publication. No. 2010/0048964, WO 2009/132220, and U.S. Patent Application No. 2010/0003716. In the present invention an IPP isomerase capable of converting to IPP to DMAPP is not limited to converting IPP to DMAPP, but may also convert DMAPP to IPP.

In the present invention, a suitable phosphatase enzyme has an enzymatic activity for cleaving a pyrophosphate from IPP or cleaving a single phosphate multiple times from IPP. In some embodiments, phosphatases that are members of the Nudix hydrolase superfamily or haloacid dehalogenase (HAD) superfamily are employed. In the present invention, a phosphatase that capable of catalyzing the dephosphorylation of dimethylallyl diphosphate (DMAPP) to 3-methyl-2-butenol is not limited to converting DMAPP to 3-methyl-2-butenol, but may also catalyze the conversion of IPP to 3-methyl-3-butenol.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

"Alga," "algal," and "microalgae" or the like, refers to plants belonging to the subphylum Algae of the phylum Thallophyta. The algae are unicellular, photosynthetic, oxygenic algae and are non-parasitis plants without roots, stems, or leaves; they contain chlorophyll and have a great variety in size, from microscopic to large seaweeds. Green algae, belonging to Eukaryota—Viridiplantae—Chlorophyta—Chlorophyceae, can be used in the invention. However, algae useful in the invention may also be blue-green, red, or brown.

Introduction

The present invention provides methods for increasing production of 3-methyl-2-butenol in a de novo synthetic pathway, in a genetically modified host cell, using isopentenyl disphosphate (IPP) as a substrate. IPP can be derived from the non-mevalonate as well as mevalonate pathways. The invention provides genetically modified cells that have been modified to be capable of expression a fusion protein that comprises an IPP isomerase fused to a phosphatase.

In a further aspect, the invention also thus provides a nucleic acid encoding a fusion protein comprising a phosphatase fused to an IPP isomerase and genetically modified host cells containing the nucleic acid such that expression of the fusion protein results in increased levels of 3-methyl-2-butenol.

The invention employs routine techniques in the field of recombinant nucleic acid technology. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-2009, Wiley Interscience).

Enzymes Present in Fusion Constructs

Phosphatases

A phosphatase, or homologous enzyme thereof, that is capable of catalyzing the dephosphorylation of IPP is employed in a fusion construct of the invention. A homologous enzyme is an enzyme that has a polypeptide sequence that is at least 70%, 75%, 80%, 85%, 90%, 95% or 99% identical to any one of the phosphatase enzymes described in this specification or in an incorporated reference. The homologous enzyme retains amino acids residues that are recognized as conserved for the enzyme and that are necessary for phosphatase activity. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

In the present invention, a suitable phosphatase enzyme has an enzymatic activity for cleaving a pyrophosphate from IPP or cleaving a single phosphate multiple times from IPP. Example of suitable phosphatase enzymes include broad specificity phosphatases, such as PhoE (YhfR) of a *Bacillus* sp., e.g., PhoE (YhfR) of *Bacillus stearothermophilus* (such as strains NGB101 and 10; Ridgen et al., *Protein Sci.* 2001, 10:1835-1846, which is incorporated in its entirety by reference), *Bacillus halodurans* (Takami et al., *Nucleic Acids Res.* (2000) 28:4317-4331, which is incorporated in its entirety by reference) or *Bacillus subtilus* (Kunst et al., *Nature* (1997), 390:249-256; Pearson et al., *J. Bacteriol.* (2000) 182:4121-4123; which are incorporated in their entireties by reference). The amino acid sequences are disclosed in Rigden et al. (*Protein Sci.* (2001) 10:1835-1846), which are incorporated in their entireties by reference. In some embodiments, the suitable phosphatase is about 190 to 210, or about 192 to 209, amino acids in length. A homologous enzyme comprises the conserved amino acid residues and sequences identified in U.S. Pat. No. 7,985,567 and in Rigden et al. (*Protein Sci.* (2001) 10:1835-1846). In some embodiments, a conserved amino acid sequence is RHG; RHGE (SEQ ID NO:1); RHGE(T or S) (SEQ ID NO:2); RHGE(T or S)(W or G)N(SEQ ID NO:3); or RHGX$_4$N (SEQ ID NO:4) (where X is any amino acid). In some embodiments, a conserved amino acid sequence is RHGEX$_3$NX$_{42}$RX$_{23}$EX$_{56-67}$H (SEQ ID NO:5) (where X is any amino acid). In some embodiments, a conserved amino acid sequence is RHGEX$_3$NX$_5$QG (SEQ ID NO:6) (where X is any amino acid). In some embodiments, a conserved amino acid sequence is RHGX$_4$NX$_{7-9}$DX$_2$LX$_3$G (SEQ ID NO:7) (where X is any amino acid). Further conserved amino acid sequences of the phosphatase are shown in FIG. 1 of Rigden et al. (*Protein Sci.* (2001) 10:1835-1846).

Two exemplary enzyme superfamilies with members able to catalyze the hydrolysis of phosphoester bonds are Nudix (Mildvan et al, *Arch. Biochem. Biophysics* (2005) 433:129) and haloacid dehalogenase (HAD) (Allen and Dunaway-Mariano, *Trends Biochem. Sci.* (2004) 29:495). (see Table 1). Another superfamily able to hydrolyze phosphoester bonds is the cofactor-dependent phosphoglycerate mutase (Rigden et al., *J. Mol. Biol.* (2003) 324:411). Other protein families able to dephosphorylate IPP and DMAPP can be used with the current invention.

In some embodiments suitable phosphatases are members of the Nudix hydrolase superfamily from, but not limited to, *Escherichia* sp., *Bacillus* sp., *Pseudomonas* sp., *Lactococcus* sp., *Caulobacter* sp., *Agrobacterium* sp., *Synechocytis* sp., *Streptomyces* sp., *Saccharomyces* sp., human, and mouse. An exemplar nucleic acid sequence of Nudix hydrolase family is found at GenBank accession No. NP_009669. In some embodiments the Nudix superfamily recognizes the general substrate motif nucleoside diphosphate linked to another moiety. In some embodiments the Nudix enzymes have a conserved 23-amino acid catalytic motif (Nudix box), consisting of the consensus sequence $GX_5EX_5[UA]XREX_2EEXGU$ (SEQ ID NO:8), where U is an aliphatic, hydrophobic residue and X is any amino acid (McLennan, A. G., *Cell Mol. Life Sci.* (2006) 63:123). There also exist individuals in the superfamily with slightly altered consensus residues. Examples of Nudix hydrolases from *E. coli* are listed in Table 1, but are not intended to limit the scope of the present invention.

In some embodiments suitable phosphatases are members of the halocid dehalogenase (HAD) superfamily from, but not limited to, *Escherichia* sp., *Bacillus* sp., *Pseudomonas* sp., *Lactococcus* sp., *Caulobacter* sp., *Agrobacterium* sp., *Synechocytis* sp., *Streptomyces* sp., *Saccharomyces* sp., human, and mouse. HADs have 10-30% sequence similarity can be identified from three short conserved sequence motifs that include a conserved aspartic acid, a serine/threonine, a lysine, and a nucleophile, such as an aspartic acid or serine. The consensus sequence for the amino acid sequence motifs are disclosed in FIG. 2 of Koonin and Tatusov, *J. Mol. Biol.* (1994) 244:125; which are incorporated in their entireties by reference) and Supplementary FIG. 1 of Kuznetsova, et al., (*J. Biol. Chem.* (2006) 281:36149; which is incorporated in their entireties by reference). Examples of HADs from *E. coli* are listed in Table 1, but are not meant to limit the scope of the present invention.

TABLE 1

| Superfamily | Organism | Name |
|---|---|---|
| HAD | *E. coli* | YniC (HAD1) |
| | *E. coli* | YfbT (HAD2) |
| | *E. coli* | YieH (HAD3) |
| | *E. coli* | YihX (HAD4) |
| | *E. coli* | YjjG (HAD5) |
| | *E. coli* | YqaB (HAD6) |
| | *E. coli* | YigB (HAD7) |
| | *E. coli* | YlrG (HAD8) |
| | *E. coli* | SerB (HAD9) |
| | *E. coli* | Gph (HAD10) |
| | *E. coli* | YcjU (HAD11) |
| | *E. coli* | YbiV (HAD12) |
| | *E. coli* | YidA (HAD13) |
| | *E. coli* | YbhA (HAD14) |
| | *E. coli* | YbjI (HAD15) |
| | *E. coli* | YigL (HAD16) |
| | *E. coli* | OtsB (HAD17) |
| | *E. coli* | Cof (HAD18) |
| | *E. coli* | YedP (HAD19) |
| | *E. coli* | YaeD (HAD20) |
| | *E. coli* | HisB (HAD21) |
| | *E. coli* | YrbI (HAD22) |
| Nudix | *E. coli* | NudA (MutT) |
| | *E. coli* | NudB |
| | *E. coli* | NudC |
| | *E. coli* | NudD (Gmm) |
| | *E. coli* | NudE |
| | *E. coli* | NudF |

TABLE 1-continued

| Superfamily | Organism | Name |
|---|---|---|
| | *E. coli* | NudG |
| | *E. coli* | NudH (RppH) |
| | *E. coli* | NudI (YfaO) |
| | *E. coli* | NudJ (YmfB) |
| | *E. coli* | NudK (YffH) |
| | *E. coli* | NudL (YeaB) |

Isomerases

An IPP isomerase, or homologous enzyme thereof, that is capable of catalyzing the conversion of IPP to DMAPP is employed in a fusion construct of the invention. A homologous enzyme is an enzyme that has a polypeptide sequence that is at least 70%, 75%, 80%, 85%, 90%, 95% or 99% identical to any one of the IPP isomerase enzymes described in this specification or in an incorporated reference. The homologous enzyme retains amino acids residues that are recognized as conserved for the enzyme and that are necessary for IPP isomerase activity. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof. The structures of various IPP isomerase has been determined. The enzymes are well characterized with respect to the catalytic site and residues important for activity (see, e.g., Zhen et al., *J. Mol. Biol.* 366:1447-1458, 2007; Zhang et al., *J. Mol. Biol.* 366:1437-1446, 2007; Street, et al., *Biochemistry* 33 (14): 4212-4217, 1994; Wouters, et al., *J. Biol. Chem.* 278 (14): 11903-11908, 2003; Bonanno, et al., *Proc. Natl. Acad Sci USA* 98: 12896-12901, 2001).

An IPP isomerase encoded by a construct of the invention catalyzes the interconversion of IPP and DMAPP. IPP isomerase enzymes are classified under the E.C. number 5.3.3.2. IPP isomerases are also referred to as isopentenyl-diphosphate delta-isomerases, isopentenylpyrophosphate delta-isomerases, isopentenylpyrophosphate isomerases, and methylbutenylpyrophosphate isomerases. Any enzyme with IPP isomerase activity can be used in the fusion protein with an enzyme with phosphatase activity with any flexible peptide linker. An enzyme with IPP isomerase activity can be either Type I or Type II. Type I are commonly found in Eukaryota and Eubacteria, such as (but not limited to) *Escherichia coli, Saccharomyces cerevisiae, Homo sapiens, Salmonella enterica, Arabidopsis thaliana, Bacillus subtilis, Rhodobacter capsulatus, Citrobacter rodentium, Klebsiella pneumoniae, Enterobacter asburiae, Pichia pastoris*. Type I IPP isomerases utilize a divalent metal (typically $Mn^{2+}$, $Mg^{2+}$, or $Ca^{2+}$). in a protonation-deprotonation reaction. Type II IPP isomerases are commonly found in Archaea and some bacteria, such as (but not limited to) *Synechocystis* sp., *Methanothermobacter thermautotrophicus, Sulfolobus shibatae, Streptomyces* sp., *Staphylococcus aureus*. Type II enzymes employ reduced flavin and metal cofactors (e.g., $Mn^{2+}$, $Mg^{2+}$, or $Ca^{2+}$).

Examples of Type I IPP isomerases that can be used in the invention, include, but are not limited to, the sequences identified by the following accession numbers: *Escherichia coli* (NP_417365), *Saccharomyces cerevisiae* (NP_015208),

*Homo sapiens* (NP_004499), *Mus musculus* (NP_663335), *Salmonella enterica* (NP_806649), *Arabidopsis thaliana* (NP_197148), *Bacillus subtilis* (NP_390168), *Caenorhabditis elegans* (NP_498766), *Streptomyces coelicolor* (NP_630823). In some embodiments, the Type I isomerase is from bacteria or a fungus, such as a yeast.

Examples of Type II IPP isomerases that can be used in the invention, include, but are not limited to, the sequences identified by the following accession numbers: *Synechocystis* sp. (NP_441701), *Methanothermobacter thermautotrophicus* (NP_275191), *Sulfolobus solfataricus* (NP_341634), and *Staphylococcus aureus* (NP_375459).

Figure 3:
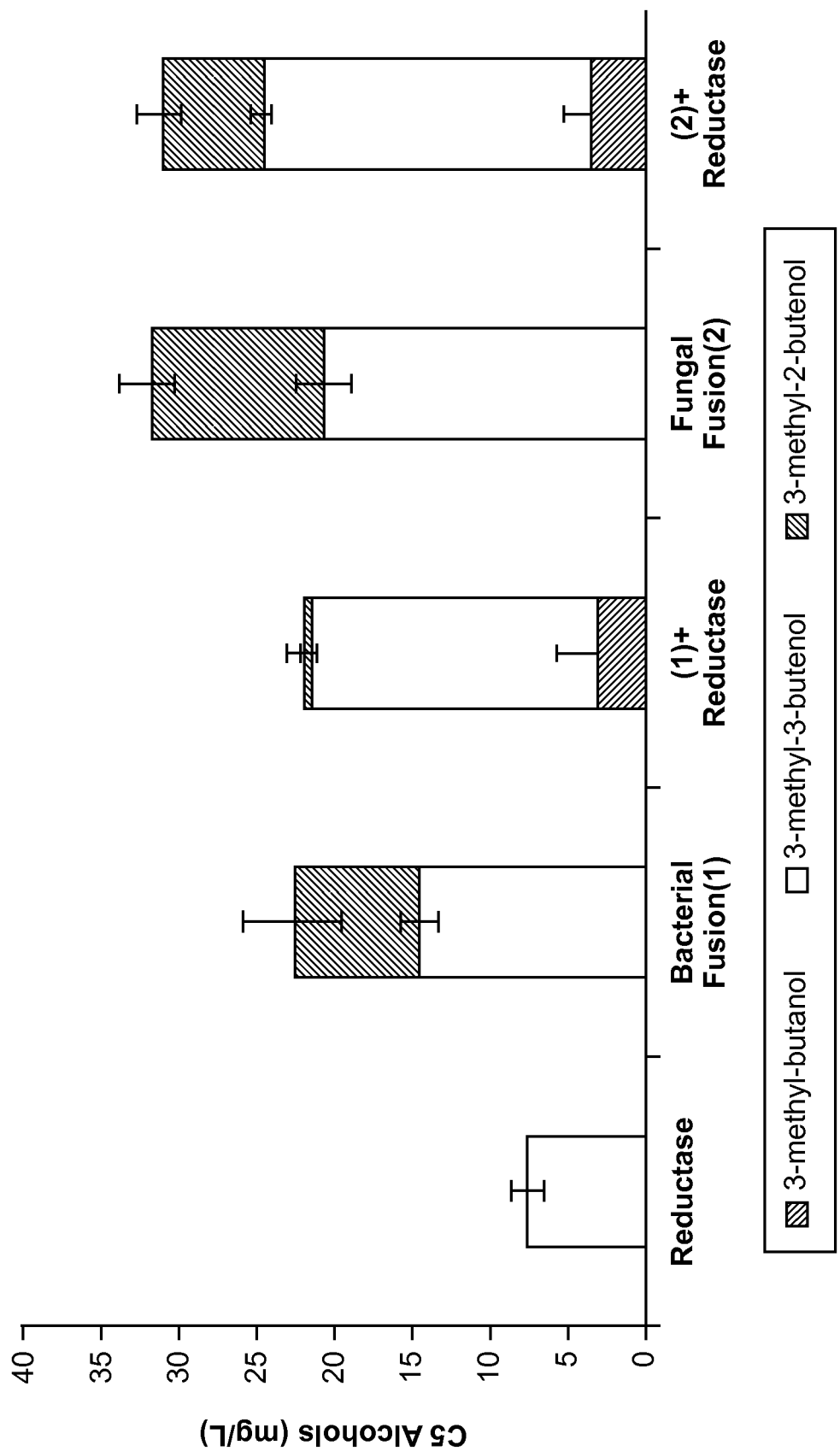
FIG. 3 provides data showing that fusion proteins in which a phosphatase is fused of an isopentyl diphosphate isomerase (IDI) increases production of 3-methyl-3-butenol in the presence of IDI, and leads to production of 3-methyl-2-butenol.

Additional examples of IPP isomerases suitable for use in the invention include those shown in in the sequence alignment FIG. 3 of Bonanno et al. *Proc. Natl. Acad. Sci. USA* 98: 12896-12901, 2001.

In some embodiments, an IPP isomerase for use in the invention, e.g., encoded by an idi gene such as an *E. coli* or *Saccharomyces* idi1 gene, require one $Mn^{2+}$ or $Mg^{2+}$ ion in its active site to fold into an active conformation and also contains a sequence related to the Nudix motif, a highly conserved 23-residue block ($GX_5EX_7REUXEEXGU$ (SEQ ID NO:9), where X is any residue and U=I, L or V), that functions as a metal binding and catalytic site. In some embodiments, an IPP isomerase protein comprised by a fusion protein of the inventio contains a similar conserved motif Gly-$X_3$-Ala-X2-Arg-Arg/Lys-ϕ-$X_2$-Glu-Leu-Gly-ϕ (SEQ ID NO:10) (see, e.g., Bonanno et al. *Proc. Natl. Acad. Sci USA* 98: 12896-12901, 2001). The metal binding site is present within the active site and plays structural and catalytical roles. As explained above, IPP isomerases are well represented in several bacteria, archaebacteria and eukaryotes, including fungi, mammals and plants. Despite sequence variations (mainly at the N-terminus), the core structure is highly conserved.

Constructs

The nucleic acid constructs of the present invention comprise fusion proteins encoding a phosphatase and an IPP isomerase. The nucleic acids encoding the fusion protein is operably linked to a promoter and optionally, additional control sequences, such that the subject fusion protein is expressed in a host cell cultured under suitable conditions. The promoters and control sequences employed in generating a nucleic acid construct encoding a fusion protein of the invention are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For example, in direct chemical synthesis, oligonucleotides of up to about 40 bases are individually synthesized, then joined (e.g., by enzymatic or chemical ligation methods, or polymerase-mediated methods) to form essentially any desired continuous sequence. Further, commercial services are available that can supply synthetic genes of the desired sequence.

In addition, the desired sequences may be isolated from natural sources using well known cloning methodology, e.g., employing PCR to amplify the desired sequences and join the amplified regions, e.g., using overlap extension to obtain a gene encoding an isomerase/phosphatase fusion protein of the invention.

The iosmerase and phosphate sequence in the recombinant fusion protein are typically joined via a linker domain.

Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val, Ala, and Thr residues and are well known in the art. The linker sequence may generally be from 1 to about 50 amino acids in length, e.g., 3, 4, 6, or 10 amino acids in length, but can be 100 or 200 amino acids in length. Useful linkers include glycine-serine polymers including, for example, (GGGGS)n (SEQ ID NO:11), (GS)n, (GSGGS)n (SEQ ID NO:12), and (GGGS)n (SEQ ID NO:13), where n is an integer of at least one; glycine-alanine polymers; alanine-serine polymers; and other flexible linkers. Linker sequences may not be required when the first and second polypeptides have non-essential N-terminal amino acid regions that can be used to separate the functional domains and prevent steric interference. In some embodiments, proline residues are incorporated into the linker to prevent the formation of significant secondary structural elements by the linker.

The nucleic acid sequence encoding the desired fusion construct comprising the isomerase and phosphatase enzyme can be incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming E. coli with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of acetyl-CoA, a starting material for IPP and DMAPP synthesis is ensured. When added, the intermediate is present in an excess amount in the culture medium.

As the host cell grows and/or multiplies, expression of the fusion protein comprising the phosphatase and isomerase is effected. Once expressed, the enzyme activities comprised by the fusion proteins catalyze the steps necessary for converting IPP to DMAPP and converting IPP/and/or DMAPP into 3-methyl-3 butenol and 3-methyl-2-butenol. In some embodiments, the host cells further comprise an enzyme encoding a reductase to convert 3-methyl-2 butenol into 3-methyl butanol. If an intermediate has been introduced, the expressed enzymes catalyze those steps necessary to convert the intermediate into the respective IPP and/or DMAPP. Any means for recovering the 5-carbon alcohol, e.g., 3-methyl-2-butenol or 3-methyl butanol from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

Host Cells

The host cells of the present invention are genetically modified in that a nucleic acid encoding a fusion protein comprising an IPP isomerase and phosphatase is introduced into the cell. In some embodiments, the IPP isomerase and/or phosphatase may be from the same species as the host cell. In other embodiments, the IPP isomerase and/or phosphatase may be from a different species. The suitable host cell is one capable of expressing a nucleic acid construct encoding an enzyme capable of catalyzing the isomerization of IPP to DMAPP and the dephosphorylation of IPP and/or DMAPP. Such a host cell may also be capable of reducing 3-methyl-2-butanol into 3-methyl butanol. In some embodiments, the host cell naturally produces IPP and/or DMAPP, and optionally may comprises heterologous nucleic acid constructs capable of expressing one or more genes for producing IPP and/or DMAPP. The gene may be heterogous to the host cell or the gene may be native to the host cell but is operatively linked to a heterologous promoter and one or more control regions which result in a higher expression of the gene in the host cell. In other embodiments, the host cell does not naturally produce IPP and/or DMAPP, and comprises heterologous nucleic acid constructs capable of expressing one or more genes for producing IPP and/or DMAPP.

The phosphatase enzyme capable of catalyzing the dephosphorylation of IPP and/or DMAPP can be native or heterologous to the host cell. Similarly, the IPP isomerase capable of converting IPP to DMAPPs can be native or heterologous to the host cell.

The host cells produce the DMAPP that is converted by the isomerase into IPP and/or DMAPP that is dephosphorylated into 3-methyl-3-buten-1-ol and/or 3-methyl-2-buten-1-ol, respectively. The host cell comprises the genes encoding enzymes in the pathway from which the IPP and/or DMAPP are synthesized from acetyl-CoA. Optionally, the host cell may comprise a gene encoding the enzyme that reduces 3-methyl-2-buten-1-ol into 3-methyl-butan-1-ol. These genes can either be native to the host cell or are heterologous to the host cell and introduced all or in part into the host cell either by integration into the host cell chromosome(s) or an expression vector, or both. In embodiments in which the host cell is modified to express a reductase to convert 3-methyl-2-butenol into 3-methyl-butanol, suitable reducatase genes are described in U.S. Pat. No. 7,985,567, which is incorporated by reference.

The host cells may comprise systems for synthesizing IPP and/or DMAPP. Such systems are taught in U.S. Pat. Nos. 7,172,886 and 7,183,089, and U.S. Pat. Application Pub. No. 2003/0148479, 2006/0079476, 2007/0077616, 2007/0092931, and 2007/0099261, which are incorporated in their entireties by reference. Such methods include producing an IPP and/or DMAPP in a genetically modified host cell, such as E. coli.

The host cells may express pyrophosphases which hydrolyze the isoprenyl diphosphate intermediates to the corresponding primary alcohols (Song, *Appl. Biochem. Biotechnol.* 2006, 128:149, which is incorporated in its entirety by reference). The host cells may be knocked out for or lack expression of any terpene cyclases which catalyze the formation of terpenes from diphosphate intermediates.

IPP and DMAPP are generated in vivo via either the mevalonate pathway or the non-mevalonate pathway (also known as the DXP pathway), which is described in Reiling et al., *Biotechnol. Bioeng.* 87(2):200-212 (2004), which is incorporated in its entirety by reference.

In some embodiments, a host cell may naturally be capable of hydrogenating the double bond of 3-methyl-2-butenol. Such a host cell may not be modified in order to be able to produce 3-methyl-butanol from 3-methyl-2-butenol or the gene encoding the enzyme for catalyzing this reaction can be modified so that expression of the enzyme is increased. A host cell that may not require modification is *Saccharomyces cerevisiae*. Gramatica et al. (*Experientia* 38, 1982) have shown that *S. cerevisiae* is capable of reducing geraniol to R-(+)-citronellol. Gramatica et al. (*J Org. Chem.* 50, 1985) have shown that *S. cerevisiae* is capable of hydrogenating the double bonds in α- or β-methyl-α,β-unsaturated aldehydes (including alcohols and acetals). Yeast can catalyze the conversion of 3-methyl-2-butenol to isopentanol (see, e.g., U.S. Pat. No. 7,985,567).

Any prokaryotic or eukaryotic host cell may be used in the present method so long as it remains viable after being transformed with a sequence of nucleic acids. Generally, although not necessarily, the host microorganism is bacterial. Examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus*, and *Paracoccus* taxonomical classes. In some embodiments, the microorganism is a cyanobacteria. In some embodiments the bacterial host is *Synechocystis* sp. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, algal, fungal, insect or mammalian cells. In some embodiments, suitable fungal cells are yeast cells, such as yeast cells of the *Saccharomyces* genus. In some embodiments the eukaryotic cell is a green algae. In some embodiments the eukaryotic cell is *Chlamydomonas reinhardtii, Scenedesmus obliquus, Chlorella vulgaris* or *Dunaliella salina*.

The host cell can further be modified to comprise endogenous solvent efflux system such as AcrAB-TolC (Ramos et al., *Annu Rev Microbiol* 2002, 56:743, which is incorporated in its entirety by reference) to pump the 5-carbon alcohol produced by the host cell out of the cell. When the host cell is capable of pumping the produced 5-carbon alcohol out of the cell, the 5-carbon alcohol can be recovered by removal of the supernatant in which the host cell is being cultured.

The toxicity of the branched-C5 alcohols will not be problematic for the viability of host cells during fermentation. The minimum inhibitory concentration (MIC) of the alcohols is approximately 1% (w/v) for *E. coli*. The branched-C5 alcohols begin to phase separate at this concentration from the growth medium.

Isolation of 5-Carbon Alcohols Produced

The present invention provides for an isolated 5-carbon alcohol produced from the method of the present invention. Isolating the 5-carbon alcohol involves the separating at least part or all of the host cells, and parts thereof, from which the 5-carbon alcohol was produced, from the isolated 5-carbon alcohol. The isolated 5-carbon alcohol may be free or essentially free of impurities formed from at least part or all of the host cells, and parts thereof. The isolated 5-carbon alcohol is essentially free of these impurities when the amount and properties of the impurities do not interfere in the use of the 5-carbon alcohol as a fuel, such as a fuel in a combustion reaction. These host cells are specifically cells that do not in nature produce the 5-carbon alcohol. The impurities are no more than 5%, 1%, 0.5%, 0.1%, 0.05%, or 0.01% by weight of a composition comprising one or more of the 5-carbon alcohols.

The present invention also provides for a combustible composition comprising an isolated 5-carbon alcohol and cellular components, wherein the cellular components do not substantially interfere in the combustion of the composition. The cellular components include whole cells or parts thereof. The cellular components are derived from host cells which produced the 5-carbon alcohol was derived.

The 5-carbon alcohol of the present invention are useful as fuels as chemical source of energy that can be used as an alternative to petroleum derived fuels, ethanol and the like.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, accession numbers, and publications mentioned herein are hereby incorporated by reference in their entireties.

The invention having been described, the following examples are offered to illustrate the subject invention by way of illustration, not by way of limitation.

EXAMPLES

The following examples are provided by way of illustration only and not by way of limitation. Those of skill in the art will readily recognize a variety of non-critical parameters that could be changed or modified to yield essentially similar results.

Example 1

Expression of Fusion Proteins in *E. coli*

Figure 2:
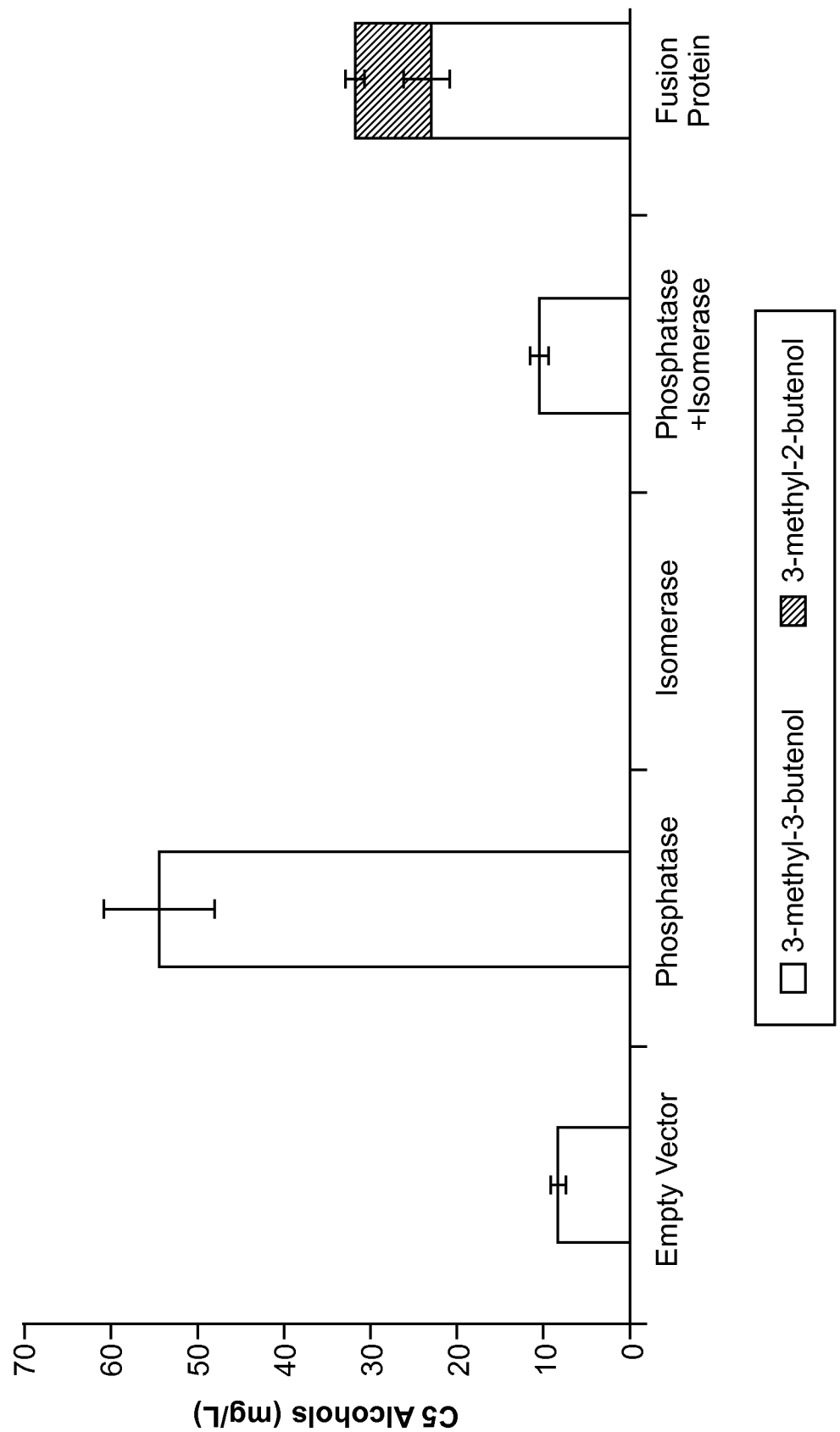
FIG. 2 provides data showing that independent expression of a heterologous IPP isomerase reduces the production of 3-methyl-3-butenol.

FIG. 2 provides data showing that expression of IPP isomerase can reduce the production of 3-methyl-3-butenol such that little or no 3-methyl-2-butenol is observed. This example demonstrates that fusion proteins comprising a phosphatase fused to an IPP isomerase results in enhanced production of 3-methyl-2-butenol.

Materials and Methods

Strains and Media

All solvents, standards, and antibiotics (e.g. tetracycline, chloramphenicol, ampicillin) were purchased from Sigma-Aldrich (St. Louis, Mo.) unless otherwise indicated. 3-methyl-3-butenol, 3-methyl-2-butenol and 3-methyl-butanol were purchased from Tokyo Chemical Industry (Portland, Oreg.). Phusion polymerase was purchased from Finnzymes (Lafayette, Colo.). All restriction enzymes were purchased from Fermentas (Glen Burnie, Md.). All primers were ordered from Integrated DNA Technologies (Coralville, Iowa).

Construction of Fusion Proteins.

The fusion protein comprises of an IPP isomerase and a phosphatase (e.g. such as a phsophatase described in U.S. Pat. No. 7,985,567) fused by a short peptide linker. In the present example, two versions of the fusion protein was made—one fungal and one bacterial. The fungal fusion protein was made by amplifying idi1 from *S. cerevisiae* and nudB from *E. coli*, and fusing the two genes with a 45-nucleotide linker (5'-GGAGGCGGTAGTGGTGGTG-GAACCGGTGGAGGCAGTGGTGGAGGC-3' (SEQ ID NO:14)) using SOEing PCR and standard cloning protocols. The bacterial fusion protein was made by amplifying idi from *E. coli* and nudB from *E. coli*, and fusing the two genes with a 57-nucleotide linker (5'-GGTGGCGGAAGTGGAG-GCGGTAGTGGTGGTGGAACCGGTGGAGGCAGTG-GTGGAG GC-3' (SEQ ID NO:15)) using SOEing PCR and standard cloning protocols. The fusion proteins were cloned into pTrc99A or pTrc99A-nemA, and co-expressed with pMevT and pMevB (see, e.g., U.S. Pat. No. 7,985,567).

For the IPP isomerases, idi1 was amplified from *S. cerevisiae* genomic DNA using the primers 5'-GGC CCATGGCTGCCGACAACAATAGTATGC-3' (SEQ ID NO:16) and 5'-GGC GAATTCTTATAGCATTCTATGAATTTGCCTGTC-3' (SEQ ID NO:17), and idi was amplified from *E. coli* genomic DNA using the primers 5'-GGC CCATGGAAACGGAACACGTCATTTT-3' (SEQ ID NO:18) and 5'-GGC GAATTCTTATTTAAGCTGGGTAAATGCAG-3' (SEQ ID NO:19). The isomerases were inserted into the NcoI-EcoRI sites (underlined in the primer sequences) of pTrc99A to construct pTrc99A-idi1 and pTrc99A-idi. nudB was amplified from *E. coli* genomic DNA using the primers primers 5'-GGCCCATGGAGGATAAAGTGTATAAGCG-3' (SEQ ID NO:20) and 5'-GGC GAATTCTCAGGCAGCGTTAATTACAAACT-3' (SEQ ID NO:21), and the gene was inserted into the NcoI-EcoRI sites (underlined in the primer sequences) of pTrc99A to construct pTrc99A-nudB. The reductase nemA from *E. coli* (see, U.S. Pat. No. 7,985,567) was amplified using the primers 5'-GGC GGATCCGGAGGACAGCTAAATGTCATCTGAAAAACTGTAAA-3' (SEQ ID NO:22) and 5'-GGC TCTAGATTACAACGTCGGGTAATCGG-3' (SEQ ID NO:23), and inserted into the BamHI-XbaI sites (underlined in the primer sequences) of pTrc99A to construct pTrc99A-nemA.

To construct the fungal fusion protein, idi1 was amplified from pTrc99A-idi1 using the primers 5'-GGC GAATTCTAGCTTTCCCCGTCTACAATTTCTTCAAGATGAC-3' (SEQ ID NO:24) and 5'-TCCACCGGTTCCACCACCAC-TACCGCCTCCTTTAAGCTGGGTAAATGC-3' (SEQ ID NO:25), nudB was amplified from pTrc99A-nudB using the primers 5'-GGTGGTGGAACCGGTGGAGGCAGTG-GTGGAGGCATGGAGGATAAAGTGTAT-3' (SEQ ID NO:26) and 5'-GGC GGTACCTCAGGCAGCGTTAATTACAAACT-3' (SEQ ID NO:27), and the PCR products from those two reactions were used for SOEing PCR using the primers 5'-GGC GAATTCTAGCTTTCCCCGTCTACAATTTCTTCAAGATGAC-3' (SEQ ID NO:28) and 5'-GGC GGTACCTCAGGCAGCGTTAATTACAAACT-3' (SEQ ID NO:29). To construct the bacterial fusion protein, idi was amplified from pTrc99A-idi using the primers 5'-GGC GAATTCATAAATCGAACACGTTTAGGAAGGAGCGCAACGATGCAAACGG CGTC-3' (SEQ ID NO:30) and 5'-ACCGGTTCCACCAC-CACTACCGCCTCCACTTCCGCCACCIT-TAAGCTGGGTAAATGC-3' (SEQ ID NO:31), nudB was amplified from pTrc99A-nudB using the primers 5'-AGTG-GTGGTGGAACCGGTGGAGGCAGTGGTGGAG-GCATGGAGGATAAAGTG-3' (SEQ ID NO:32) and 5'-GGCGGTACCTCAGGCAGCGTTAATTACAAACT-3' (SEQ ID NO:33), and the PCR products from those two reactions were used for SOEing PCR using the primers 5'-GGC GAATTCATAAATCGAACACGTTTAGGAAGGAGCGCAACGATGCAAACGG CGTC-3' (SEQ ID NO:34) and 5'-GGC GGTACCTCAGGCAGCGTTAATTACAAACT-3' (SEQ ID NO:35). The part of each primer that is associated with the nucleotide linker is in italics. The fungal and bacterial fusion proteins were inserted into the EcoRI-KpnI sites (underlined in the primer sequences) of pTrc99A and pTrc99A-nemA.

Quantification of Alcohol Production.

Overnight cultures were inoculated into EZ-Rich Defined Medium with 0.2% glucose and grown for 4 hours at 37° C. Afterwards, the cultures were induced with 0.1 mM IPTG and grown at 30° C. for 18-20 hours shaking at 200 r.p.m. 700 µl of sample was analyzed by mixing it with 700 µl of extraction solvent (80:20 chloroform:methanol spiked with 50 mg $l^{-1}$ of butanol internal standard). The samples were vortexed for 15 minutes and centrifuged for 1 minute at 12000 r.p.m. 450 µl of the organic layer was removed from each sample and transferred to a clean GC vial for analysis.

The GC-FID data were collected using a Tr-Wax column (0.25 mm×30 m, 0.25 µm film thickness; Thermo Electron) on a Focus GC with TriPlus autosampler (Thermo Electron). The carrier was set at constant pressure for 300 kPa, and the inlet temperature was set to 200° C. The oven program was as follows: 40° C. (1.50 min hold); 40-110° C. (15° C. $min^{-1}$). Samples were normalized using the butanol internal standard and quantified using authentic standards.

The expression systems comprising the phosphatase/isomerase fusion proteins exhibited increased production of 3-methyl-2-butenol from 3-methyl-3 butenol compared to the other constructs. The bacterial variant recovered 50% of production, whereas the fungal variant recovered 60% of production (compared to production in the absence of an isomerase), and produced significant levels of 3-methyl-2-butenol. In this experiment, the fungal variant produced 3-methyl-3-butenol and 3-methyl-2-butenol in a 2:1 ratio. Expression of a reductase able to catalyze the reduction of 3-methyl-2-butenol led to the production of 3-methyl-buta-nol. The ratio of the alcohols produced with the fungal variant of the fusion protein is 2:1:1 3-methyl-3-butenol:3-methyl-2-butenol:3-methyl-butanol. Approximately half of the 3-methyl-2-butenol is converted to 3-methyl-butanol.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A genetically modified host cell transformed with a nucleic acid construct encoding a fusion protein comprising a phosphatase capable of catalyzing the dephosphorylation of dimethylallyl diphosphate (DMAPP) linked to an isopentyl pyrophosphate (IPP) isomerase capable of converting IPP to DMAPP, wherein the nucleic acid construct is operably linked to a promoter.

2. The genetically modified host cell of claim 1, wherein the genetically modified host cell further comprises a nucleic acid encoding a reductase that is capable of converting 3-methyl-2-butenol to 3-methy-butanol.

3. The genetically modified host cell of claim 2, wherein the reductase is encoded by a nucleic acid construct introduced into the cell.

4. The genetically modified host cell of claim 1, wherein the IPP isomerase is a Type I isomerase.

5. The genetically modified host cell of claim 4, wherein the IPP isomerase is encoded by the *E. coli* idi gene or the *Saccharomyces cerevisiae* idil gene.

6. The genetically modified host cell of claim 1, wherein the phosphatase is a member of the Nudix superfamily.

7. The genetically modified host cell of claim 6, wherein the phosphatase is encoded by the *E. coli* nudB gene.

8. The genetically modified host cell of claim 1, wherein the host cell is a prokaryotic cell selected from *Escherichia, Enterobacter, Azotobacter, Erwinia, Bacillus, Pseudomonas, Klebsielia, Proteus, Salmonella, Serratia, Shigella, Rhizobia*, Vitreoscilla, Synechococcus, *Synechocystis*, or *Paracoccus* taxonomical classes.

9. The genetically modified host cell of claim 8, wherein the prokaryotic cell is an *Escherichia coli* cell.

10. The genetically modified host cell of claim 1, wherein the host cell is a fungal cell.

11. The genetically modified host cell of claim 10, wherein the fungal cell is a yeast cell.

12. The genetically modified host cell of claim 11, wherein the yeast cell is a *Saccharomyces* sp. cell.

13. The genetically modified host cell of claim 1, wherein the host cell is an algal, insect or mammalian cell line.

14. The genetically modified host cell of claim 1, wherein the IPP isomerase is encoded by the *E. coli* idi gene or the *Saccharomyces cerevisiae* idil gene; and the phosphatase is encoded by the *E. coli* nudB gene.

15. The genetically modified host cell of claim 14, wherein the host cell is a prokaryotic cell.

16. The genetically modified host cell of claim 15, wherein the host cell is a prokaryotic cell selected from *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, or *Paracoccus* taxonomical classes.

17. The genetically modified host cell of claim 15, wherein the prokaryotic cell is an *Escherichia coli* cell.

18. A method of enhancing production of a 3-methyl-2-butenol, the method comprising culturing a genetically modified host cell transformed with a nucleic acid construct encoding a fusion protein comprising a phosphatase capable of catalyzing the dephosphorylation of DMAPP linked to IPP isomerase capable of converting IPP to DMAPP, wherein the nucleic acid construct is operably linked to a promoter, under conditions such that the culturing results in the expression of the fusion protein and production of 3-methyl-2-butenol.

19. The method of claim 18, further comprising recovering 3-methyl-2-butenol produced by the genetically modified host cell.

20. The method of claim 18, wherein the genetically modified host cell further comprises a nucleic acid encoding a reductase such that expression of the reductase converts 3-methyl-2-butenol to 3-methyl butanol.

21. The method of claim 20, wherein the reductase is encoded by a nucleic acid construct introduced into the genetically modified host cell.

22. The method of claim 20, further comprising recovering 3-methyl-2-butenol or 3-methyl butanol produced by the genetically modified host cell.

23. The method of claim 18, wherein the IPP isomerase is a Type I isomerase.

24. The method of claim 23, wherein the IPP isomerase is encoded by the *E. coli* idi gene or the *Saccharomyces cerevisiae* idil gene.

25. The method of claim 18, wherein the phosphatase is a member of the Nudix superfamily.

26. The method of claim 25, wherein the phosphatase is encoded by the *E. coli* nudB gene.

27. The method of claim 18, wherein the genetically modified host cell is a prokaryotic cell selected from *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, or *Paracoccus* taxonomical classes.

28. The method of claim 27, wherein the prokaryotic cell is an *Escherichia coli* cell.

29. The method of claim 18, wherein the genetically modified host cell is a fungal cell.

30. The method of claim 29, wherein the fungal cell is a yeast cell.

31. The method of claim 30, wherein the yeast cell is a *Saccharomyces* sp. cell.

32. The method of claim 18, wherein the genetically modified host cell is an algal, insect or mammalian cell line.

33. The method of claim 18, wherein the IPP isomerase is encoded by the *E. coli* idi gene or the *Saccharomyces cerevisiae* idil gene; and the phosphatase is encoded by the *E. coli* nudB gene.

34. The method of claim 33, wherein the genetically modified host cell is a prokaryotic cell.

35. The method of claim 34, wherein the prokaryotic cell is selected from *Escherichia, Enterobacter, Azotobacter, Erwinia, Bacillus, Pseudomonas, Klebsielia, Proteus, Salmonella, Serratia, Shigella, Rhizobia*, Vitreoscilla, Synechococcus, *Synechocystis*, or *Paracoccus* taxonomical classes.

36. The method of claim 34, wherein the prokaryotic cell is an *Escherichia coli* cell.

* * * * *

SEQUENCE LISTING

```
<160> NUMBER OF SEQ ID NOS: 35

<210> SEQ ID NO 1
<211> LENGTH: 4
<212> TYPE: PRT
<213> ORGANISM: Artificial Sequence
<220> FEATURE:
<223> OTHER INFORMATION: synthetic phosphatase conserved amino acid
      sequence

<400> SEQUENCE: 1

Arg His Gly Glu
 1

<210> SEQ ID NO 2
<211> LENGTH: 5
<212> TYPE: PRT
<213> ORGANISM: Artificial Sequence
<220> FEATURE:
<223> OTHER INFORMATION: synthetic phosphatase conserved amino acid
      sequence
<220> FEATURE:
<221> NAME/KEY: VARIANT
<222> LOCATION: (5)...(5)
<223> OTHER INFORMATION: Xaa = Thr or Ser

<400> SEQUENCE: 2

Arg His Gly Glu Xaa
 1               5

<210> SEQ ID NO 3
<211> LENGTH: 7
<212> TYPE: PRT
<213> ORGANISM: Artificial Sequence
<220> FEATURE:
<223> OTHER INFORMATION: synthetic phosphatase conserved amino acid
      sequence
<220> FEATURE:
<221> NAME/KEY: VARIANT
<222> LOCATION: (5)...(5)
<223> OTHER INFORMATION: Xaa = Thr or Ser
<220> FEATURE:
<221> NAME/KEY: VARIANT
<222> LOCATION: (6)...(6)
<223> OTHER INFORMATION: Xaa = Trp or Gly

<400> SEQUENCE: 3

Arg His Gly Glu Xaa Xaa Asn
 1               5

<210> SEQ ID NO 4
<211> LENGTH: 8
<212> TYPE: PRT
<213> ORGANISM: Artificial Sequence
<220> FEATURE:
<223> OTHER INFORMATION: synthetic phosphatase conserved amino acid
      sequence
<220> FEATURE:
<221> NAME/KEY: VARIANT
<222> LOCATION: (4)...(7)
<223> OTHER INFORMATION: Xaa = any amino acid

<400> SEQUENCE: 4

Arg His Gly Xaa Xaa Xaa Xaa Asn
 1               5

<210> SEQ ID NO 5
<211> LENGTH: 143
<212> TYPE: PRT
```

```
<213> ORGANISM: Artificial Sequence
<220> FEATURE:
<223> OTHER INFORMATION: synthetic phosphatase conserved amino acid
      sequence
<220> FEATURE:
<221> NAME/KEY: VARIANT
<222> LOCATION: (5)...(131)
<223> OTHER INFORMATION: Xaa = any amino acid
<220> FEATURE:
<221> NAME/KEY: VARIANT
<222> LOCATION: (132)...(142)
<223> OTHER INFORMATION: Xaa = any amino acid, may be present or absent

<400> SEQUENCE: 5

Arg His Gly Glu Xaa Xaa Xaa Asn Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Arg Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Glu Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa His
    130                 135                 140

<210> SEQ ID NO 6
<211> LENGTH: 15
<212> TYPE: PRT
<213> ORGANISM: Artificial Sequence
<220> FEATURE:
<223> OTHER INFORMATION: synthetic phosphatase conserved amino acid
      sequence
<220> FEATURE:
<221> NAME/KEY: VARIANT
<222> LOCATION: (5)...(13)
<223> OTHER INFORMATION: Xaa = any amino acid

<400> SEQUENCE: 6

Arg His Gly Glu Xaa Xaa Xaa Asn Xaa Xaa Xaa Xaa Xaa Gln Gly
 1               5                  10                  15

<210> SEQ ID NO 7
<211> LENGTH: 25
<212> TYPE: PRT
<213> ORGANISM: Artificial Sequence
<220> FEATURE:
<223> OTHER INFORMATION: synthetic phosphatase conserved amino acid
      sequence
<220> FEATURE:
<221> NAME/KEY: VARIANT
<222> LOCATION: (4)...(15)
<223> OTHER INFORMATION: Xaa = any amino acid
<220> FEATURE:
<221> NAME/KEY: VARIANT
<222> LOCATION: (16)...(17)
<223> OTHER INFORMATION: Xaa = any amino acid, may be present or absent
<220> FEATURE:
<221> NAME/KEY: VARIANT
<222> LOCATION: (19)...(24)
```

```
<223> OTHER INFORMATION: Xaa = any amino acid

<400> SEQUENCE: 7

Arg His Gly Xaa Xaa Xaa Xaa Asn Xaa Xaa Xaa Xaa Xaa Xaa Xaa
  1               5                  10                  15

Xaa Asp Xaa Xaa Leu Xaa Xaa Xaa Gly
             20                  25

<210> SEQ ID NO 8
<211> LENGTH: 23
<212> TYPE: PRT
<213> ORGANISM: Artificial Sequence
<220> FEATURE:
<223> OTHER INFORMATION: synthetic catalytic motif (Nudix box) conserved
      23-amino acid consensus sequence
<221> NAME/KEY: VARIANT
<222> LOCATION: (2)...(12)
<223> OTHER INFORMATION: Xaa = any amino acid
<220> FEATURE:
<221> NAME/KEY: VARIANT
<222> LOCATION: (13)...(13)
<223> OTHER INFORMATION: Xaa = an aliphatic, hydrophobic amino acid or
      Ala
<220> FEATURE:
<221> NAME/KEY: VARIANT
<222> LOCATION: (14)...(21)
<223> OTHER INFORMATION: Xaa = any amino acid
<220> FEATURE:
<221> NAME/KEY: VARIANT
<222> LOCATION: (23)...(23)
<223> OTHER INFORMATION: Xaa = an aliphatic, hydrophobic amino acid

<400> SEQUENCE: 8

Gly Xaa Xaa Xaa Xaa Xaa Glu Xaa Xaa Xaa Xaa Xaa Xaa Xaa Arg Glu
  1               5                  10                  15

Xaa Xaa Glu Glu Xaa Gly Xaa
             20

<210> SEQ ID NO 9
<211> LENGTH: 23
<212> TYPE: PRT
<213> ORGANISM: Artificial Sequence
<220> FEATURE:
<223> OTHER INFORMATION: synthetic conserved 23-residue block sequence
      metal binding and catalytic site related to Nudix motif
<220> FEATURE:
<221> NAME/KEY: VARIANT
<222> LOCATION: (2)...(14)
<223> OTHER INFORMATION: Xaa = any amino acid
<220> FEATURE:
<221> NAME/KEY: VARIANT
<222> LOCATION: (17)...(17)
<223> OTHER INFORMATION: Xaa = Ile, Leu or Val
<220> FEATURE:
<221> NAME/KEY: VARIANT
<222> LOCATION: (18)...(21)
<223> OTHER INFORMATION: Xaa = any amino acid
<220> FEATURE:
<221> NAME/KEY: VARIANT
<222> LOCATION: (23)...(23)
<223> OTHER INFORMATION: Xaa = Ile, Leu or Val

<400> SEQUENCE: 9

Gly Xaa Xaa Xaa Xaa Xaa Glu Xaa Xaa Xaa Xaa Xaa Xaa Xaa Arg Glu
  1               5                  10                  15

Xaa Xaa Glu Glu Xaa Gly Xaa
             20

<210> SEQ ID NO 10
<211> LENGTH: 16
```

```
<212> TYPE: PRT
<213> ORGANISM: Artificial Sequence
<220> FEATURE:
<223> OTHER INFORMATION: synthetic IPP isomerase metal binding site
      conserved motif
<220> FEATURE:
<221> NAME/KEY: VARIANT
<222> LOCATION: (2)...(7)
<223> OTHER INFORMATION: Xaa = any amino acid
<220> FEATURE:
<221> NAME/KEY: VARIANT
<222> LOCATION: (9)...(9)
<223> OTHER INFORMATION: Xaa = Arg or Lys
<220> FEATURE:
<221> NAME/KEY: VARIANT
<222> LOCATION: (10)...(10)
<223> OTHER INFORMATION: Xaa = unknown
<220> FEATURE:
<221> NAME/KEY: VARIANT
<222> LOCATION: (11)...(12)
<223> OTHER INFORMATION: Xaa = any amino acid
<220> FEATURE:
<221> NAME/KEY: VARIANT
<222> LOCATION: (16)...(16)
<223> OTHER INFORMATION: Xaa = unknown

<400> SEQUENCE: 10

Gly Xaa Xaa Xaa Ala Xaa Xaa Arg Xaa Xaa Xaa Xaa Glu Leu Gly Xaa
 1               5                  10                  15

<210> SEQ ID NO 11
<211> LENGTH: 5
<212> TYPE: PRT
<213> ORGANISM: Artificial Sequence
<220> FEATURE:
<223> OTHER INFORMATION: synthetic glycine-serine polymer flexible
      linker
<220> FEATURE:
<221> NAME/KEY: PEPTIDE
<222> LOCATION: (1)...(5)
<223> OTHER INFORMATION: positions 1-5 may be repeated an undefined
      number of times, (GGGGS)n

<400> SEQUENCE: 11

Gly Gly Gly Gly Ser
 1               5

<210> SEQ ID NO 12
<211> LENGTH: 5
<212> TYPE: PRT
<213> ORGANISM: Artificial Sequence
<220> FEATURE:
<223> OTHER INFORMATION: synthetic glycine-serine polymer flexible
      linker
<220> FEATURE:
<221> NAME/KEY: PEPTIDE
<222> LOCATION: (1)...(5)
<223> OTHER INFORMATION: positions 1-5 may be repeated an undefined
      number of times, (GSGGS)n

<400> SEQUENCE: 12

Gly Ser Gly Gly Ser
 1               5

<210> SEQ ID NO 13
<211> LENGTH: 4
<212> TYPE: PRT
<213> ORGANISM: Artificial Sequence
<220> FEATURE:
<223> OTHER INFORMATION: synthetic glycine-serine polymer flexible
      linker
<220> FEATURE:
<221> NAME/KEY: PEPTIDE
```

```
<222> LOCATION: (1)...(4)
<223> OTHER INFORMATION: positions 1-4 may be repeated an undefined
      number of times, (GGGS)n

<400> SEQUENCE: 13

Gly Gly Gly Ser
 1

<210> SEQ ID NO 14
<211> LENGTH: 45
<212> TYPE: DNA
<213> ORGANISM: Artificial Sequence
<220> FEATURE:
<223> OTHER INFORMATION: synthetic IPP isomerase and phosphatase fungal
      fusion protein 45-nucleotide linker

<400> SEQUENCE: 14
ggaggcggta gtggtggtgg aaccggtgga ggcagtggtg gaggc                45

<210> SEQ ID NO 15
<211> LENGTH: 57
<212> TYPE: DNA
<213> ORGANISM: Artificial Sequence
<220> FEATURE:
<223> OTHER INFORMATION: synthetic E. coli idi and nudB bacterial fusion
      protein 57-nucleotide linker and phosphatase
      fungal fusion protein 45-nucleotide linker

<400> SEQUENCE: 15
ggtggcggaa gtggaggcgg tagtggtggt ggaaccggtg gaggcagtgg tggaggc    57

<210> SEQ ID NO 16
<211> LENGTH: 30
<212> TYPE: DNA
<213> ORGANISM: Artificial Sequence
<220> FEATURE:
<223> OTHER INFORMATION: synthetic S. cerevisiae IPP isomerase idi1
      amplification primer

<400> SEQUENCE: 16
ggcccatggc tgccgacaac aatagtatgc                                 30

<210> SEQ ID NO 17
<211> LENGTH: 36
<212> TYPE: DNA
<213> ORGANISM: Artificial Sequence
<220> FEATURE:
<223> OTHER INFORMATION: synthetic S. cerevisiae IPP isomerase idi1
      amplification primer

<400> SEQUENCE: 17
ggcgaattct tatagcattc tatgaatttg cctgtc                          36

<210> SEQ ID NO 18
<211> LENGTH: 28
<212> TYPE: DNA
<213> ORGANISM: Artificial Sequence
<220> FEATURE:
<223> OTHER INFORMATION: synthetic E. coli isomerase idi amplification
      primer

<400> SEQUENCE: 18
ggcccatgga aacggaacac gtcatttt                                   28

<210> SEQ ID NO 19
<211> LENGTH: 32
<212> TYPE: DNA
```

<213> ORGANISM: Artificial Sequence
<220> FEATURE:
<223> OTHER INFORMATION: synthetic E. coli isomerase idi amplification primer

<400> SEQUENCE: 19
ggcgaattct tatttaagct gggtaaatgc ag                32

<210> SEQ ID NO 20
<211> LENGTH: 28
<212> TYPE: DNA
<213> ORGANISM: Artificial Sequence
<220> FEATURE:
<223> OTHER INFORMATION: synthetic E. coli nudB amplification primer

<400> SEQUENCE: 20
ggcccatgga ggataaagtg tataagcg                28

<210> SEQ ID NO 21
<211> LENGTH: 32
<212> TYPE: DNA
<213> ORGANISM: Artificial Sequence
<220> FEATURE:
<223> OTHER INFORMATION: synthetic E. coli nudB amplification primer

<400> SEQUENCE: 21
ggcgaattct caggcagcgt taattacaaa ct                32

<210> SEQ ID NO 22
<211> LENGTH: 42
<212> TYPE: DNA
<213> ORGANISM: Artificial Sequence
<220> FEATURE:
<223> OTHER INFORMATION: synthetic E. coli reductase nemA amplification primer

<400> SEQUENCE: 22
ggcggatccg gaggacagct aaatgtcatc tgaaaaactg ta                42

<210> SEQ ID NO 23
<211> LENGTH: 29
<212> TYPE: DNA
<213> ORGANISM: Artificial Sequence
<220> FEATURE:
<223> OTHER INFORMATION: synthetic E. coli reductase nemA amplification primer

<400> SEQUENCE: 23
ggctctagat tacaacgtcg ggtaatcgg                29

<210> SEQ ID NO 24
<211> LENGTH: 56
<212> TYPE: DNA
<213> ORGANISM: Artificial Sequence
<220> FEATURE:
<223> OTHER INFORMATION: synthetic pTrc99A-idi1 idi1 amplification primer

<400> SEQUENCE: 24
ggcgaattct agctttcccc gtctacaatt tcttcaagat gactgccgac aacaat                56

<210> SEQ ID NO 25
<211> LENGTH: 48
<212> TYPE: DNA
<213> ORGANISM: Artificial Sequence
<220> FEATURE:
<223> OTHER INFORMATION: synthetic pTrc99A-idi1 idi1 amplification

```
                                     primer

<400> SEQUENCE: 25
tccaccggtt ccaccaccac taccgcctcc tttaagctgg gtaaatgc                 48

<210> SEQ ID NO 26
<211> LENGTH: 51
<212> TYPE: DNA
<213> ORGANISM: Artificial Sequence
<220> FEATURE:
<223> OTHER INFORMATION: synthetic pTrc99A-nudB nudB amplification
      primer

<400> SEQUENCE: 26
ggtggtggaa ccggtggagg cagtggtgga ggcatggagg ataaagtgta t             51

<210> SEQ ID NO 27
<211> LENGTH: 32
<212> TYPE: DNA
<213> ORGANISM: Artificial Sequence
<220> FEATURE:
<223> OTHER INFORMATION: synthetic pTrc99A-nudB nudB amplification
      primer

<400> SEQUENCE: 27
ggcggtacct caggcagcgt taattacaaa ct                                  32

<210> SEQ ID NO 28
<211> LENGTH: 56
<212> TYPE: DNA
<213> ORGANISM: Artificial Sequence
<220> FEATURE:
<223> OTHER INFORMATION: synthetic idi1 and nudB SOEing PCR primer

<400> SEQUENCE: 28
ggcgaattct agctttcccc gtctacaatt tcttcaagat gactgccgac aacaat        56

<210> SEQ ID NO 29
<211> LENGTH: 32
<212> TYPE: DNA
<213> ORGANISM: Artificial Sequence
<220> FEATURE:
<223> OTHER INFORMATION: synthetic idi1 and nudB SOEing PCR primer

<400> SEQUENCE: 29
ggcggtacct caggcagcgt taattacaaa ct                                  32

<210> SEQ ID NO 30
<211> LENGTH: 60
<212> TYPE: DNA
<213> ORGANISM: Artificial Sequence
<220> FEATURE:
<223> OTHER INFORMATION: synthetic pTrc99A-idi idi amplification primer

<400> SEQUENCE: 30
ggcgaattca taaatcgaac acgtttagga aggagcgcaa cgatgcaaac ggaacacgtc    60

<210> SEQ ID NO 31
<211> LENGTH: 57
<212> TYPE: DNA
<213> ORGANISM: Artificial Sequence
<220> FEATURE:
<223> OTHER INFORMATION: synthetic pTrc99A-idi idi amplification primer

<400> SEQUENCE: 31
accggttcca ccaccactac cgcctccact tccgccacct ttaagctggg taaatgc       57
```

```
<210> SEQ ID NO 32
<211> LENGTH: 51
<212> TYPE: DNA
<213> ORGANISM: Artificial Sequence
<220> FEATURE:
<223> OTHER INFORMATION: synthetic pTrc99A-nudB nudB amplification
      primer

<400> SEQUENCE: 32
agtggtggtg gaaccggtgg aggcagtggt ggaggcatgg aggataaagt g            51

<210> SEQ ID NO 33
<211> LENGTH: 32
<212> TYPE: DNA
<213> ORGANISM: Artificial Sequence
<220> FEATURE:
<223> OTHER INFORMATION: synthetic pTrc99A-nudB nudB amplification
      primer

<400> SEQUENCE: 33
ggcggtacct caggcagcgt taattacaaa ct                                 32

<210> SEQ ID NO 34
<211> LENGTH: 60
<212> TYPE: DNA
<213> ORGANISM: Artificial Sequence
<220> FEATURE:
<223> OTHER INFORMATION: synthetic idi and nudB SOEing PCR primer

<400> SEQUENCE: 34
ggcgaattca taaatcgaac acgtttagga aggagcgcaa cgatgcaaac ggaacacgtc   60

<210> SEQ ID NO 35
<211> LENGTH: 32
<212> TYPE: DNA
<213> ORGANISM: Artificial Sequence
<220> FEATURE:
<223> OTHER INFORMATION: synthetic idi and nudB SOEing PCR primer

<400> SEQUENCE: 35
ggcggtacct caggcagcgt taattacaaa ct                                 32
```